(12) United States Patent
Mahmoud

(10) Patent No.: US 7,770,466 B2
(45) Date of Patent: Aug. 10, 2010

(54) METHOD FOR MEASURING STENT DISLODGEMENT FORCE

(75) Inventor: Tamer M. Mahmoud, Cupertino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 77 days.

(21) Appl. No.: 12/167,048

(22) Filed: Jul. 2, 2008

(65) Prior Publication Data

US 2010/0000328 A1    Jan. 7, 2010

(51) Int. Cl.
*G01N 3/08*    (2006.01)

(52) U.S. Cl. .......................................... 73/826; 73/760

(58) Field of Classification Search .................. 73/760, 73/73, 826–854
See application file for complete search history.

(56) References Cited

U.S. PATENT DOCUMENTS

| 4,721,507 | A  | * | 1/1988  | Chin ..................... 604/100.02 |
| 4,820,298 | A  | * | 4/1989  | Leveen et al. .............. 623/1.18 |
| 4,890,611 | A  | * | 1/1990  | Monfort et al. ............. 606/159 |
| 5,546,646 | A  | * | 8/1996  | Williams et al. ......... 29/407.08 |
| 7,344,505 | B2 | * | 3/2008  | Stofer et al. ................ 600/561 |
| 7,347,822 | B2 | * | 3/2008  | Brockway et al. ........... 600/486 |
| 2004/0230289 | A1 | * | 11/2004 | DiMatteo et al. ........... 623/1.13 |
| 2007/0038292 | A1 | * | 2/2007  | Danielpour ................ 623/1.42 |
| 2007/0162106 | A1 | * | 7/2007  | Evans et al. ................ 623/1.23 |

* cited by examiner

*Primary Examiner*—Max Noori
(74) *Attorney, Agent, or Firm*—Fulwider Patton LLP

(57) ABSTRACT

A method for measuring the force necessary to dislodge a stent from a balloon catheter to which it is mounted. The balloon catheter with a stent mounted thereon is encased in a mass of gel material. The force necessary to pull the catheter from the gel is measured.

16 Claims, 4 Drawing Sheets

METHOD FOR MEASURING STENT DISLODGEMENT FORCE

The present invention is directed to a method of measuring the force necessary to dislodge a stent from a catheter on which it is mounted and more particularly pertains to generating a more accurate measurement of such force than has heretofore been possible.

BACKGROUND

In order to deliver a stent to a deployment site within a patient, the stent is crimped onto a balloon catheter which is then advanced along a guide wire through the patient's vasculature. Once in position, the balloon is temporarily inflated to expand and thereby deploy the stent. Any combination of frictional, mechanical and/or adhesive forces may be relied upon to maintain the stent in position on the balloon prior to deployment as the catheter is advanced through the vasculature. It is essential for the stent remain precisely positioned on the balloon even while being advanced along a tortuous path as any misalignment relative to the balloon can be problematic during expansion. Quantification of a stent's ability to resist dislodgement is of interest for a variety of purposes including for quality control as well for the purpose of evaluating and comparing the performance of different stent and stent delivery system combinations. Previously used methods have introduced extraneous forces that have an adverse effect on the accuracy of a measurement, typically because a force normal to the stent is relied upon to grasp or retain the stent while the catheter is being pulled therefrom. Such additional force can serve to apply additional crimp to the stent and thereby artificially increase its resistance to dislodgement. The ability to more accurately and repeatably measure the force necessary to dislodge the stent from the balloon is most desirable.

SUMMARY OF THE INVENTION

The present invention provides a method for measuring the force required to dislodge a stent from the balloon catheter to which it is crimped. The method provides for an accurate and repeatable measurement of such value which is most desirable for quality control as well as for evaluation purposes. The method obviates the need to apply a force normal to the stent in order to grasp and retain the stent during the test and thereby eliminates the adverse effect such additional crimping force would have on the measured value.

The method of the present invention provides for the encasement of the balloon catheter mounted stent in a gel material. The mass of gel is then restrained as the catheter is pulled therefrom while the force necessary to displace the catheter relative to the gel material as well as the stent that is retained therein is measured. The gel serves to retain the stent without the application of any forces normal to the stent's longitudinal axis. In order to determine whether such measured force accurately reflects the dislodgement force of stent from the balloon, or more particularly, whether there is any adhesion between the gel and the balloon, an identical balloon catheter but devoid of a stent may be similarly encased in a mass of gel. The mass of gel is again restrained as the catheter is pulled therefrom while the force necessary to displace the catheter relative to the gel material is measured. If a force is measurable, the difference between the two measured forces yields the stent net dislodgement force.

These and other features and advantages of the present invention will become apparent from the following detailed description of the preferred embodiments which, taken in conjunction with the accompanying drawings, illustrate by way of example the principles of the present invention.

DETAILED DESCRIPTION OF THE PREFERRED EMBODIMENTS

The present invention provides a method for accurately measuring the stent dislodgement force. The method is used to quantify a stent's ability to remain crimped about a balloon catheter such as when the catheter is advanced through tortuous or constricted vasculature.

The method relies on a gel material to retain the stent as the balloon catheter is pulled therefrom. The force necessary to pull the catheter from the gel-retained stent is measured and compared to the force necessary to pull a similar balloon catheter sans stent mounted thereon from the gel material. The difference between the two measured forces yields the dislodgement force of the stent from the balloon.

Figure 1:
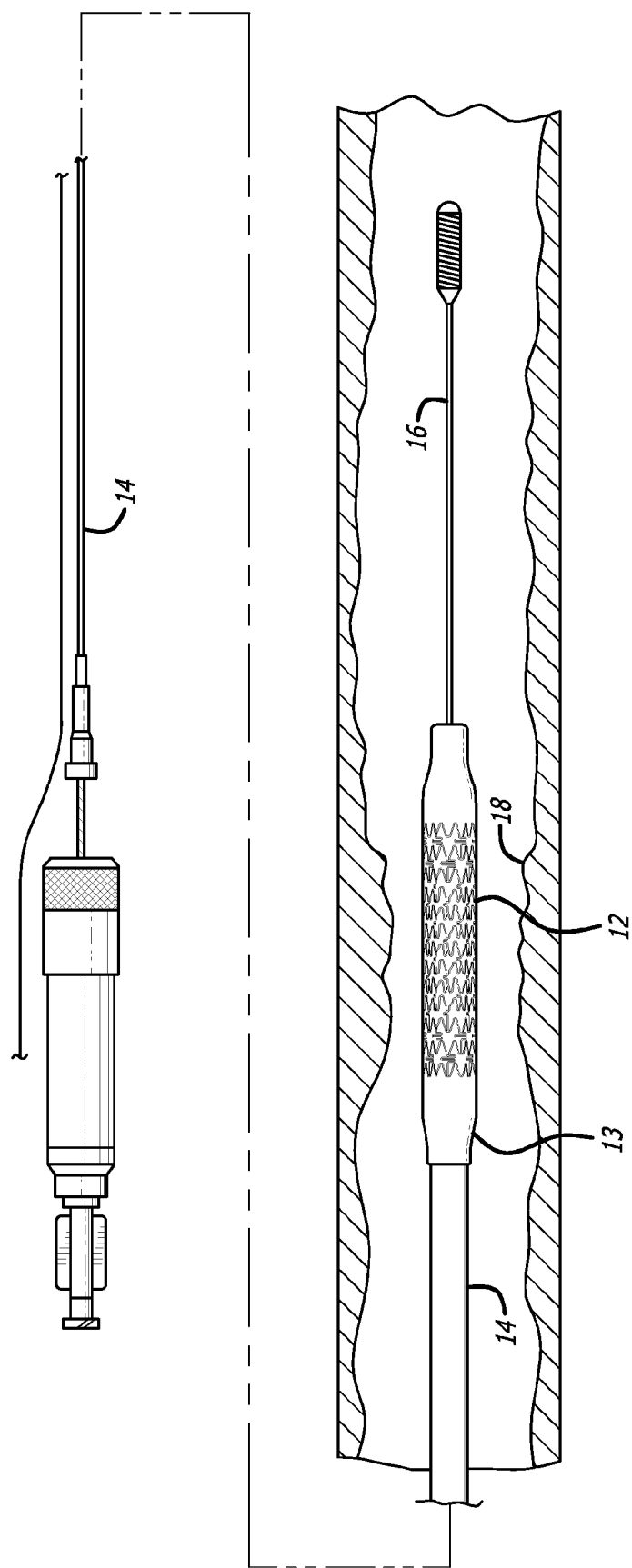
FIG. 1 is a schematic illustration of a stent and its delivery system.

FIG. 1 schematically illustrates a stent 12 mounted on the balloon 13 of a balloon catheter 14. The stent is crimped about the balloon in its deflated state. After the a guide wire 16 is maneuvered into position, the balloon catheter is advanced thereon until the stent is in position at the deployment site 18. Inflation of the balloon causes the stent to expand to engage the vessel walls. Subsequent deflation of the balloon and retraction of the catheter leaves the expanded stent in place to provide support to the vessel walls and thereby maintain patency.

The method of the present invention initially requires the balloon mounted stent to be encased in a gel material. Any of various gelling casting materials can be used in practicing the present invention including but not limited to for example urethanes, silicons, hydrogels or other. In the preferred embodiment, a solution of PVA is prepared by mixing 65 g of DMSO with 22 g of PVA and 35 g of distilled water. The solution is stirred and then brought up to temperature by placing the mixing container containing the three components in an oil bath that is maintained at 200° C. When the solution becomes translucent it is ready for use.

Figure 2:
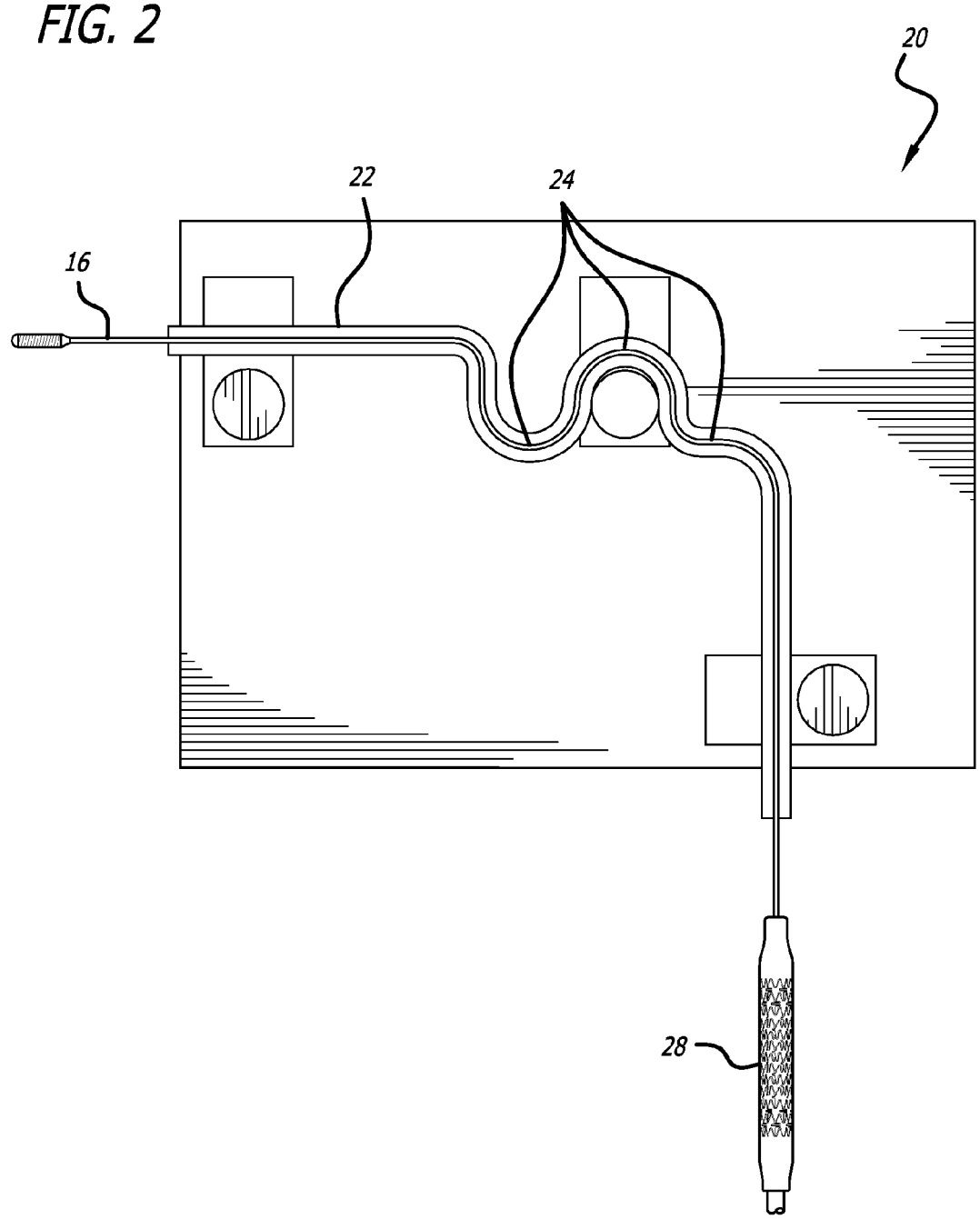
FIG. 2 is a schematic illustration of a preconditioning device for use in practicing the method of the present invention.

Prior to encasement in the PVA, the test sample is subjected to a preconditioning procedure wherein it is drawn through tortuous path such as is illustrated in FIG. 2. The preconditioning device 20 comprises a length of tubing 22 having a number of curves 24 formed therein that simulate arterial curvature. The entire fixture is submerged in a water bath that is maintained at 37° C. and the tubing is purged of any air. A guide wire 26 is extended through the tubing after which the test sample 28 (balloon catheter with stent mounted thererto or balloon catheter sans stent) is advanced on the guide wire through the tubing and then retracted therefrom. This is done at a rate of approximately 2 cm/sec and then repeated.

Figure 3:
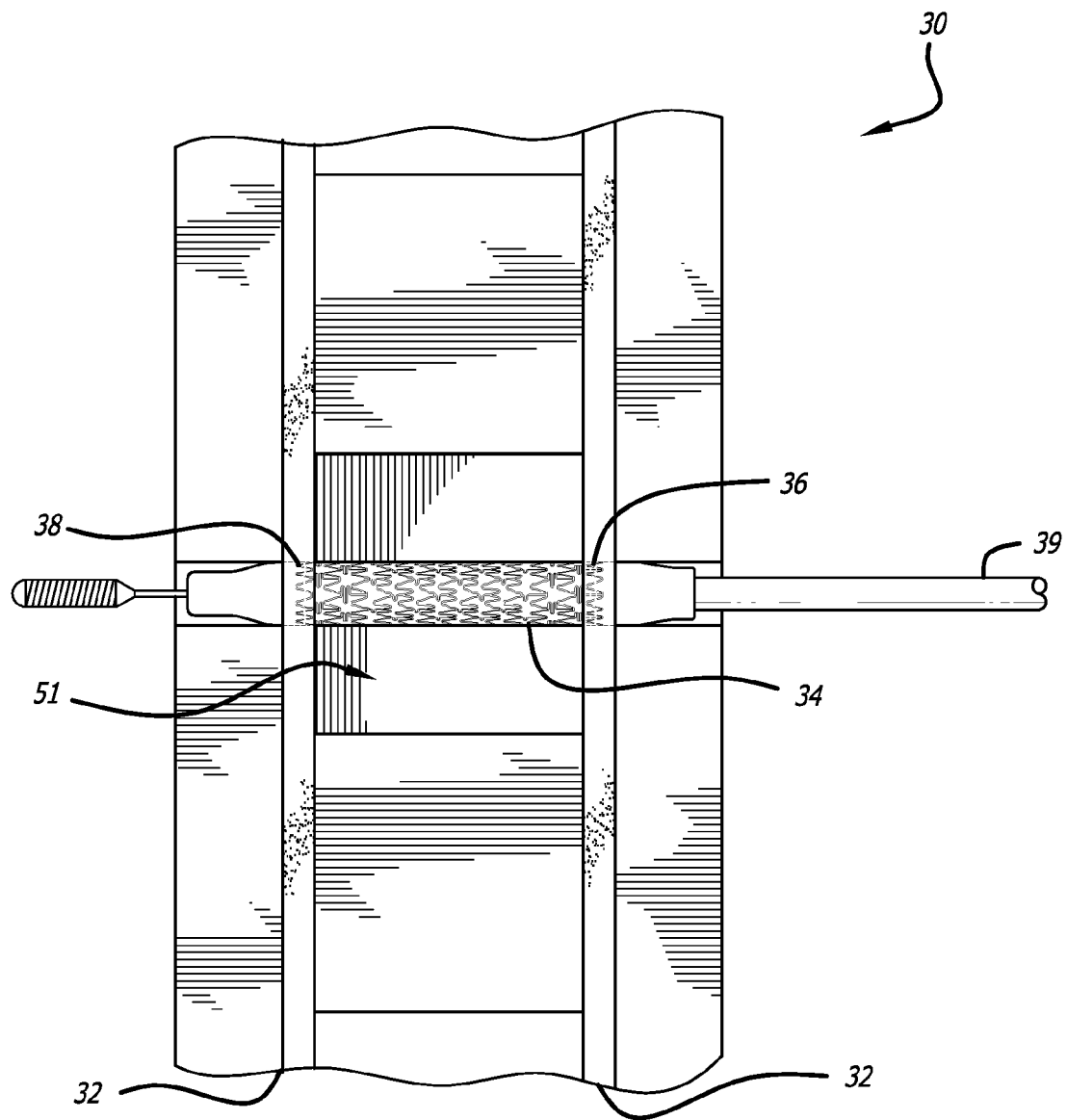
FIG. 3 is a schematic illustration of a casting mold for encasing a sample in a ge in accordance with the method of the present invention.
Figure 4:
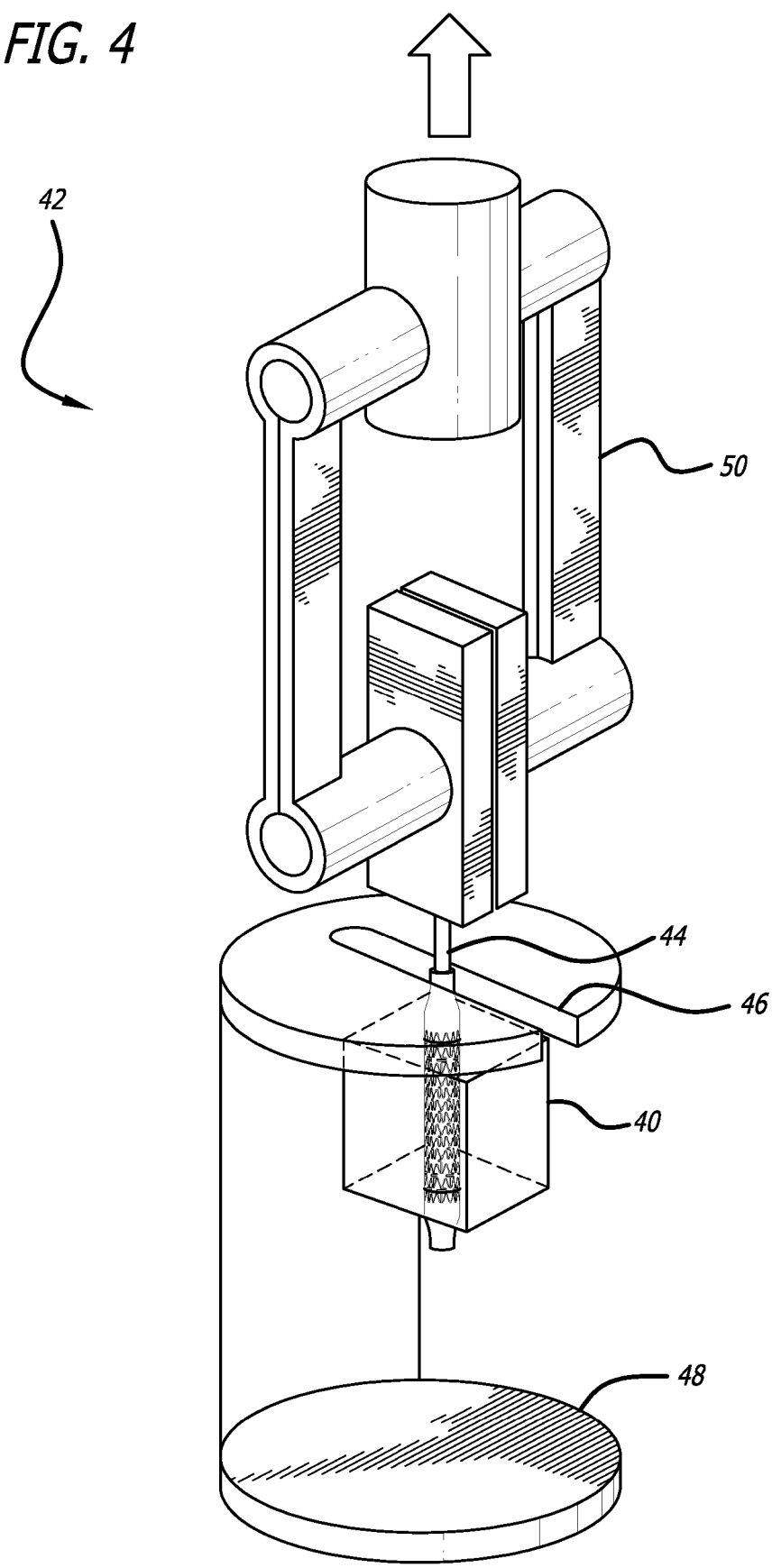
FIG. 4 is a schematic illustration of a sample fixtured in a tension testing machine in accordance with the method of the present invention.

A casting mold 30 is assembled as is schematically illustrated in FIG. 3 wherein silicone foam rubber serves as a dams 32 to keep the PVA within the confines of the mold. The dimensions of the mold are selected as a function of the length of the stent such that the mold is about 2 mm shorter than the stent. The balloon catheter mounted, preconditioned stent 34 is then inserted through small holes that are formed in the foam rubber and positioned such that the proximal 36 and distal 38 end rings of the stent are embedded in the foam and will not be cast in the PVA. A length of catheter 39 proximal to the balloon remains extending from one end of the mold. The mold may optionally be configured to allow multiple samples to be prepared simultaneously. The PVA solution is allowed to cool to about 50° C. and then poured into the molds. After approximately 3 hours, the PVA will have gelled and the sample is ready for testing.

Once the PVA has gelled, the encased test samples 40 are removed from the molds and fixtured in a tension testing machine 42 as for example manufactured by Instron of Norwood, Mass. The encased sample is oriented such that the proximal end 44 of the catheter extends upwardly through a slot 46 in the machine's lower fixture 48 while a pneumatic gripper 50 engages the length of catheter protruding from the mold. The lower fixture prevents the mass of gel from rising while the gripper exerts a tensile force on the catheter. The pulling rate is set at 1 inch/minute and the machine records force and displacement. The test is complete when the catheter has moved at least 10 mm relative to the gel and the maximum force recorded by the machine is noted. Any movement of the stent relative to the PVA voids the test.

It may additionally be desirable to determine whether any gel to balloon adhesion is contributing to the force that is measured in displacing the balloon catheter relative to the stent and gel mass. A balloon catheter sans stent is subjected to the same preconditioning, encasement and pull testing procedure. If a significant amount of force is measurable, the difference between the maximum force recorded for the catheter without the stent is subtracted from the maximum force recorded for the catheter with the stent mounted thereon to yield the net dislodgement force. Once it is determined that a particular gel/balloon material combination is not subject to any significant adhesion, this portion of the testing procedure may be eliminated.

While a particular form of the invention has been illustrated and described, it will be apparent to those skilled in the art that various modifications can be made without departing from the spirit and scope of the invention. Accordingly, it is not intended that the invention be limited except by the appended claims.

What is claimed is:

1. A method for measuring a force necessary to dislodge a stent from a balloon of a balloon catheter on which it is mounted, comprising:
    encasing said stent in a mass of gel such that a length of catheter extends from said mass of gel;
    restraining said mass of gel;
    subjecting said length of catheter extending from said mass of gel to a tensile force; and
    measuring the tensile force exerted as said catheter is displaced relative to said stent.

2. The method of claim 1, wherein said measured tensile force is the maximum tensile force exerted during said displacement.

3. The method of claim 1, wherein said stent has a proximal and a distal end ring and said end rings are not encased in said mass of gel.

4. The method of claim 1, wherein said balloon mounted stent is preconditioned by advancing and retracting said balloon mounted stent through a tortuosity.

5. The method of claim 4, wherein said preconditioning is performed at 37° C.

6. The method of claim 1, wherein said mass of gel comprises PVA.

7. The method of claim 6, wherein said mass of gel is formed by mixing DMSO, PVA, and distilled water in a ratio of 65:22:35 by weight.

8. The method of claim 1, further comprising:
    encasing a balloon of a second balloon catheter devoid of a stent, wherein said second balloon is identical to said balloon catheter on which said stent is mounted, in a second mass of gel such that a length of said second catheter extends from said second mass of gel;
    restraining said second mass of gel;
    subjecting said length of catheter extending from said second mass of gel to a tensile force;
    measuring the tensile force exerted as said second catheter is displaced relative to said second mass of gel; and
    subtracting said tensile force measured as said second catheter is displaced relative to said second mass of gel from said tensile force measured as said catheter is displaced relative to said stent.

9. The method of claim 8, wherein said measured tensile forces are the maximum tensile forces exerted during said displacements.

10. The method of claim 8, wherein said stent has a proximal and a distal end ring and said end rings are not encased in said mass of gel.

11. The method of claim 8, wherein said balloon mounted stent is preconditioned by advancing and retracting said balloon mounted stent through a tortuosity.

12. The method of claim 11, wherein said preconditioning is performed at 37° C.

13. The method of claim 8, wherein said second balloon catheter is subjected to preconditioning by advancing and retracting said catheter through a tortuosity.

14. The method of claim 13, wherein said preconditioning of said second balloon catheter is performed at 37° C.

15. The method of claim 8, wherein said mass of gel comprises PVA.

16. The method of claim 15, wherein said mass of gel is formed by mixing DMSO, PVA and distilled water in a ratio of 65:22:35 by weight.

* * * * *